US008626291B2

(12) United States Patent
Stadler et al.

(10) Patent No.: US 8,626,291 B2
(45) Date of Patent: Jan. 7, 2014

(54) METHOD FOR DISCRIMINATING ANODAL AND CATHODAL CAPTURE

(75) Inventors: Robert W. Stadler, Shoreview, MN (US); Todd J. Sheldon, North Oaks, MN (US); Vincent E. Splett, Apple Valley, MN (US); Wade M. Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 88 days.

(21) Appl. No.: 13/192,713

(22) Filed: Jul. 28, 2011

(65) Prior Publication Data
US 2013/0030492 A1  Jan. 31, 2013

(51) Int. Cl.
*A61N 1/365* (2006.01)

(52) U.S. Cl.
USPC .............................................. 607/17; 607/28

(58) Field of Classification Search
USPC ...................... 600/508–510; 607/9, 17, 25–28
See application file for complete search history.

(56) References Cited

U.S. PATENT DOCUMENTS

| 5,117,824 | A | 6/1992 | Keimel |
|---|---|---|---|
| 5,707,398 | A | 1/1998 | Lu |
| 5,873,898 | A | 2/1999 | Hemming |
| 6,393,316 | B1 | 5/2002 | Gillberg |
| 6,477,417 | B1 | 11/2002 | Levine |
| 6,687,545 | B1 | 2/2004 | Lu |
| 6,704,598 | B2 | 3/2004 | Ding |
| 6,950,701 | B2 | 9/2005 | Begemann |
| 7,123,963 | B2 | 10/2006 | Sawchuk |
| 7,239,913 | B2 | 7/2007 | Ding |
| 7,555,336 | B2 | 6/2009 | Sheth |
| 7,697,977 | B2 | 4/2010 | Yonce |
| 2004/0172079 | A1 | 9/2004 | Chinchoy |
| 2008/0177344 | A1 | 7/2008 | Maskara |
| 2009/0030470 | A1 | 1/2009 | Holmstrom |
| 2009/0043351 | A1 | 2/2009 | Sathaye et al. |
| 2009/0043352 | A1 | 2/2009 | Brooke |
| 2010/0121396 | A1 | 5/2010 | Gill |
| 2010/0121404 | A1 | 5/2010 | Bjorling |
| 2010/0137935 | A1 | 6/2010 | Parikh |
| 2010/0262204 | A1* | 10/2010 | McCabe et al. ................. 607/17 |
| 2010/0331906 | A1 | 12/2010 | Williamson |
| 2011/0004264 | A1 | 1/2011 | Siejko et al. |
| 2011/0022111 | A1 | 1/2011 | Min |

OTHER PUBLICATIONS

Dendy KF, et al.; "Anodal stimulation: An underrecognized cause of nonresponders to cardiac resynchronization therapy"; Indian Pacing and Electrophysiology Journal, 2011, 11(3):pp. 64-72.

* cited by examiner

*Primary Examiner* — Rex R Holmes
(74) *Attorney, Agent, or Firm* — Michael C. Soldner

(57) ABSTRACT

An implantable device and associated method detect anodal capture during electrical stimulation. A first pacing pulse is delivered using a first cathode and a first anode. A second pacing pulse is delivered using the first cathode and a second anode. A first response to the first pacing pulse and a second response to the second pacing pulse are measured. Anodal capture of the first pacing pulse at the first anode is detected in response to a first difference between the first response and the second response.

26 Claims, 11 Drawing Sheets

METHOD FOR DISCRIMINATING ANODAL AND CATHODAL CAPTURE

TECHNICAL FIELD

The disclosure relates generally to medical devices for delivering electrical stimulation and, in particular, to an apparatus and method for discriminating between anodal and cathodal capture in an electrical stimulation therapy device.

BACKGROUND

In site-specific cardiac pacing methods, such as cardiac resynchronization therapy (CRT), cathodal stimulation is generally desired. In some cases, an anodal capture threshold may be lower than the cathodal capture threshold. As a result, a clinician may think that capture of a particular heart chamber is occurring at the cathode electrode site when in fact the evoked response is initiated at the anode electrode site. This change in activation sequence from an expected activation sequence of the heart may result in less benefit from a delivered therapy than intended or possible. This compromised therapeutic benefit may go unrecognized since the clinician will typically not realize that anodal capture is occurring instead of cathodal capture.

In particular, as multi-polar coronary sinus leads become commercially available for pacing and sensing in the left ventricle, anodal capture in the left ventricle can become a more common occurrence when a bipolar pair of electrodes positioned along the left ventricle is selected for pacing in the left ventricle. In CRT, anodal stimulation in the LV will result in a different activation sequence of the LV than expected. Doctors will typically select a cathode positioned at a desired pacing site, such as the near the LV base, paired with an anode that results in the lowest capture threshold to conserve pacemaker battery energy. In some cases, the selected anode may cause anodal capture only or a combination of anodal and cathodal capture. If the anode is nearer the LV apex than the base, less desired apical pacing will occur, unknown to the clinician.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Methods and associated circuitry are described herein for detecting and discriminating anodal stimulation during bipolar stimulation of a heart chamber. These methods may be implemented in any single, dual, or multi-chamber pacing device having at least two electrodes positioned for bipolar pacing in a heart chamber. More often, practice of the disclosed methods will be used when multiple electrodes are available in a paced heart chamber providing two or more bipolar electrode vectors to choose from for pacing in the heart chamber. In some embodiments, at least one electrode positioned away from the heart chamber is provided for use as an anode for obtaining measurements during unipolar pacing of the heart chamber that are used for discriminating between anodal and cathodal capture. The anode electrode may be in or along another heart chamber, along the housing of an associated IMD, or a subcutaneously implanted electrode such as a patch electrode. In some embodiments, which involve measuring conduction times between heart chambers, electrodes for sensing a conducted depolarization in a heart chamber other than the one being paced are needed. In other embodiments, a distant sensing bipole may be used to measure a conduction time within the same chamber being paced.

In the following description, a dual-chamber (biventricular) pacing device is described as one illustrative embodiment of a device that may utilize the anodal capture detection methods described herein. This device is used in particular for delivering cardiac resynchronization therapy (CRT) by pacing in one or both ventricles. It should be recognized, however, that anodal capture detection and discrimination during bipolar pacing may be implemented in numerous device configurations that include bipolar pacing capabilities in at least one heart chamber for delivering CRT or any other pacing therapy. Furthermore, aspects of the anodal capture detection and discrimination methods may be implemented in any medical device delivering electrical stimulation to excitable body tissue and are not necessarily limited to practice in cardiac pacing applications.

Figure 1:
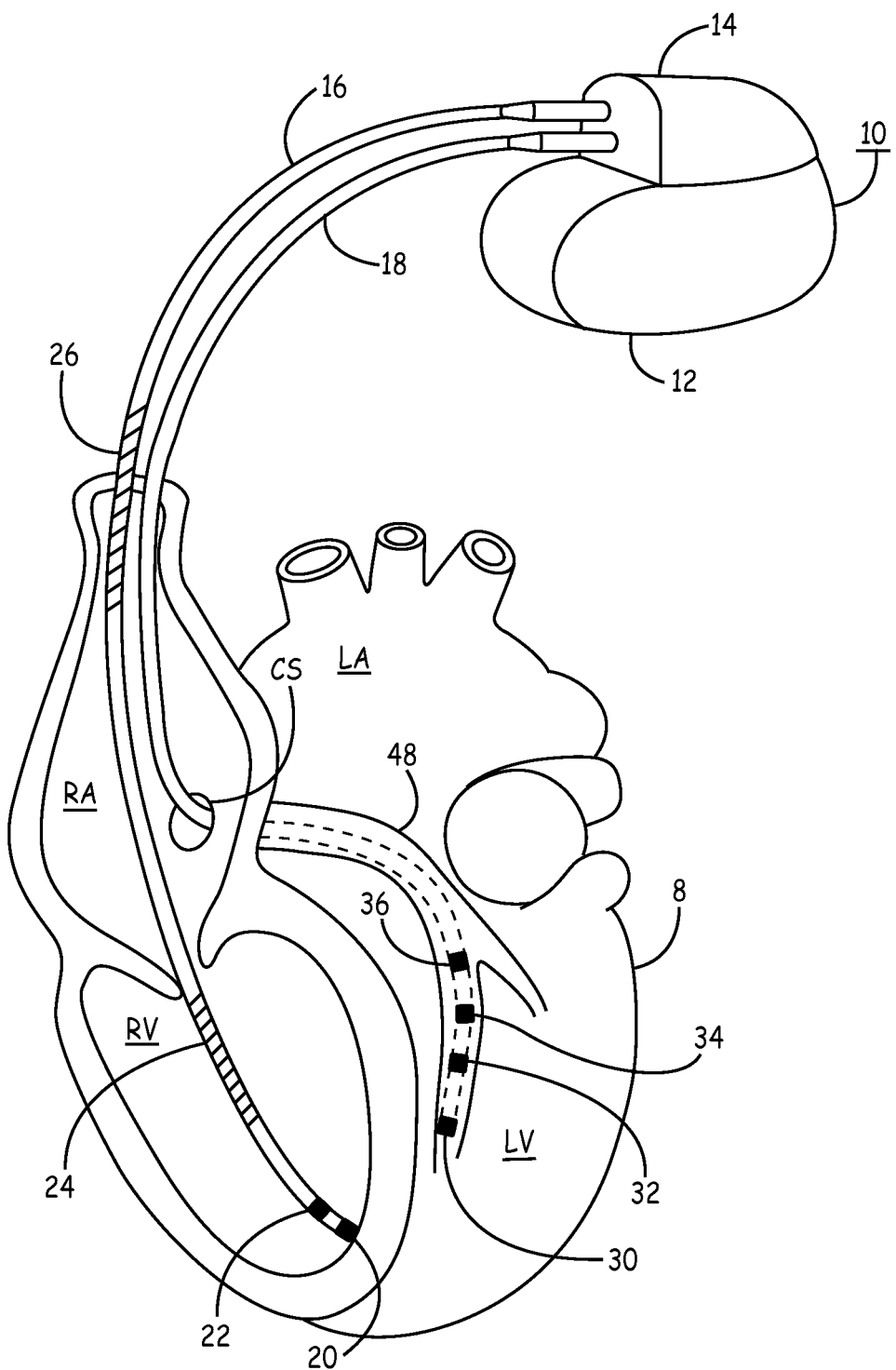
FIG. 1 depicts an implantable medical device (IMD) coupled to a patient's heart by way of a right ventricular (RV) lead and a coronary sinus (CS) lead.

FIG. 1 depicts an implantable medical device (IMD) 10 coupled to a patient's heart 8 by way of a right ventricular (RV) lead 16 and a coronary sinus (CS) lead 18. The IMD 10 is embodied as a cardiac pacing device provided for restoring ventricular synchrony by delivering pacing pulses to one or more heart chambers as needed to control the heart activation sequence. The heart 8 is shown in a partially cut-away view illustrating the upper heart chambers, the right atrium (RA) and left atrium (LA), and the lower heart chambers, the right ventricle (RV) and left ventricle (LV), and the great cardiac vein 48, which branches to form inferior cardiac veins. The great cardiac vein 48 opens into the coronary sinus (CS) in the right atrium.

The transvenous leads 16 and 18 connect IMD 10 with the RV and the LV, respectively. It is recognized that in some embodiments, additional leads and/or electrodes may be coupled to an IMD for connecting the IMD with the RA and the LA to provide sensing and/or pacing in three or all four chambers of the heart.

Each lead 16 and 18 carries pace/sense electrodes coupled to insulated, elongated conductors extending through leads 16 and 18. A remote indifferent housing electrode 12 is formed as part of the outer surface of the housing of the IMD 10. The pace/sense electrodes and the remote indifferent housing electrode 12 can be selectively employed to provide a number of unipolar and bipolar pace/sense electrode combinations for pacing and sensing functions.

RV lead 16 is shown as a transvenous, endocardial lead passed through the RA into the RV. The RV lead 16 is formed with a proximal lead connector adapted for insertion into a connector bore of IMD connector block 14. The lead connector (not shown in FIG. 1) electrically couples electrodes 20, 22, 24, and 26 carried by RV lead 16 to internal circuitry of IMD 10 via connector block 14. RV pace/sense tip electrode 20 and proximal RV pace/sense ring electrode 22 are provided for RV pacing and sensing of RV EGM signals. RV lead 16 additionally carries an RV coil electrode 24 and a superior vena cava (SVC) coil electrode 26, which may be used for delivering high-voltage cardioversion or defibrillation shocks. RV ring electrode 22, RV coil electrode 24 or SVC coil electrode 26 are used in some embodiments as an anode paired with an electrode positioned along the LV for delivering unipolar pacing pulses in the LV during anodal capture analysis.

In the illustrative embodiment, a multi-polar LV CS lead 18 is passed through the RA, into the CS and further into a cardiac vein 48 to extend the distal four pace/sense electrodes 30, 32, 34 and 36 along the LV chamber to achieve LV pacing and sensing of LV EGM signals using any combination of electrodes 30 through 36. The LV CS lead 18 is coupled at a proximal end lead connector (not shown) inserted into a bore of IMD connector block 14 to provide electrical coupling of electrodes 30 through 36 to IMD internal circuitry.

The depicted positions of the leads and electrodes shown in FIG. 1 in or about the right and left ventricles are approximate and merely illustrative. It is recognized that alternative leads and pace/sense electrodes that are adapted for placement at pacing or sensing sites on or in or relative to the RA, LA, RV and/or LV may be used in conjunction with the methods described herein. For example, in a three chamber pacing device, a RA lead may be positioned carrying a tip and ring electrode for pacing and sensing in the right atrial chamber. Additionally, in a four chamber embodiment, LV CS lead 22 could bear proximal LA CS pace/sense electrode(s) positioned along the lead body to lie adjacent the LA for use in pacing the LA or sensing LA EGM signals. A multi-chamber device in which anodal capture detection methods may be practiced is generally disclosed in U.S. Pat. No. 7,555,336 (Sheth, et al.), hereby incorporated herein by reference in its entirety.

The electrodes designated above as "pace/sense" electrodes can generally be used for both pacing and sensing functions. These "pace/sense" electrodes can be selected to be used exclusively as pace or sense electrodes or to be used for both pacing and sensing in programmed combinations for sensing cardiac signals and delivering cardiac stimulation pulses along selected sensing and pacing vectors. Separate or shared indifferent pace and sense electrodes can also be designated in pacing and sensing functions, including the use of RV coil electrode 24 and/or SVC coil electrode 26 as a pacing anode.

Figure 2:
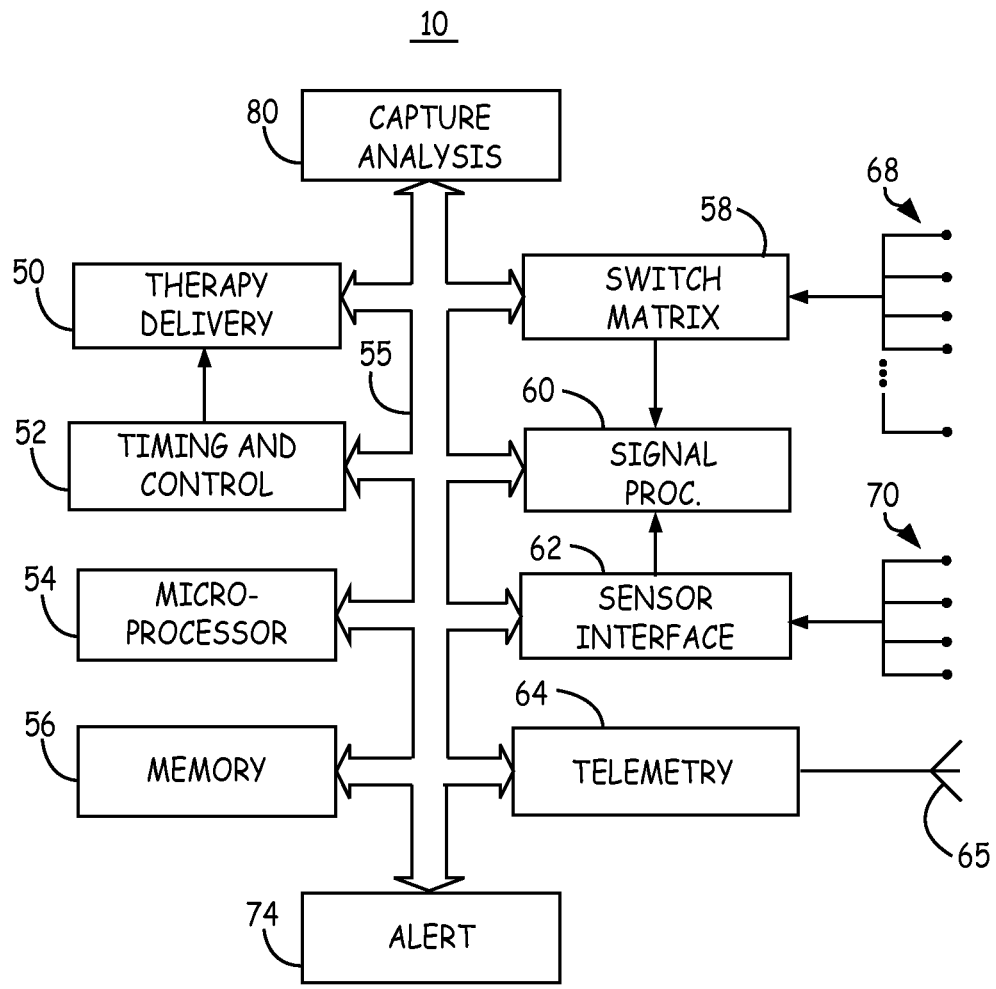
FIG. 2 is a functional block diagram of the IMD shown in FIG. 1.

FIG. 2 is a functional block diagram of IMD 10. IMD 10 generally includes timing and control circuitry 52 and an operating system that may employ microprocessor 54 or a digital state machine for timing sensing and therapy delivery functions in accordance with a programmed operating mode. Microprocessor 54 and associated memory 56 are coupled to the various components of IMD 10 via a data/address bus 55. Microprocessor 54, memory 56, timing and control 52, and capture analysis module 80 may operate cooperatively as a controller for executing and controlling various functions of IMD 10.

IMD 10 includes therapy delivery module 50 for delivering a therapy in response to determining a need for therapy based on sensed physiological signals. Therapy delivery module 50 provides electrical stimulation therapies, such as cardiac pacing or arrhythmia therapies, including CRT. Therapies are delivered by module 50 under the control of timing and control 52. Therapy delivery module 50 is typically coupled to two or more electrodes 68 via an optional switch matrix 58. Switch matrix 58 may be used for selecting which electrodes and corresponding polarities are used for delivering electrical stimulation pulses. Electrodes 68 may correspond to the electrodes shown in FIG. 1 or any electrodes coupled to IMD 10.

Therapy delivery module 50 includes an electrical pulse generator for generating pacing pulses. Timing and control 52, in cooperation with microprocessor 54 and capture analysis module 80, control the delivery of pacing pulses by therapy delivery 50 according to a capture analysis algorithm for detecting and discriminating anodal capture. The detection of anodal capture is used to select which of electrodes 68 and corresponding polarities are used in delivering a cardiac pacing therapy.

Electrodes 68 are also used for receiving cardiac electrical signals. Cardiac electrical signals may be monitored for use in diagnosing or monitoring a patient condition or may be used for determining when a therapy is needed and in controlling the timing and delivery of the therapy. When used for sensing, electrodes 68 are coupled to signal processing circuitry 60 via switch matrix 58. Signal processor 60 includes sense amplifiers and may include other signal conditioning circuitry and an analog-to-digital converter. Cardiac EGM signals (either analog sensed event signals or digitized signals or both) may then be used by microprocessor 54 for detecting physiological events, such as detecting and discriminating cardiac arrhythmias, determining activation patterns of the patient's heart, and in performing anodal capture analysis as will be described further herein.

IMD 10 may additionally be coupled to one or more physiological sensors 70. Physiological sensors 70 may include pressure sensors, accelerometers, flow sensors, blood chemistry sensors, activity sensors or other physiological sensors for use with implantable devices. Physiological sensors may be carried by leads extending from IMD 10 or incorporated in or on the IMD housing 12. Sensor interface 62 receives signals from sensors 70 and provides sensor signals to signal processing circuitry 60. Sensor signals are used by microprocessor 54 for detecting physiological events or conditions.

The operating system includes associated memory 56 for storing a variety of programmed-in operating mode and parameter values that are used by microprocessor 54. The memory 56 may also be used for storing data compiled from sensed signals and/or relating to device operating history for telemetry out upon receipt of a retrieval or interrogation instruction. A capture analysis algorithm may be stored in memory 56 and executed by microprocessor 54 and/or capture analysis module 80 with input received from electrodes 68 for detecting anodal capture. Alternatively, capture analysis module 80 may be embodied as dedicated circuitry for receiving and processing signals for detecting anodal capture and generating a report or warnings pertaining to anodal capture. Microprocessor 54 may respond to capture analysis data by altering electrode selection for delivering a cardiac pacing therapy or triggering alert 74 to generate an alert signal or message to a clinician that anodal capture is occurring. Data relating to capture analysis may be stored in memory 56 for later retrieval.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit. Telemetry circuitry 64 may be used to transmit an alert or notification generated in response to detecting anodal capture.

Figure 3:
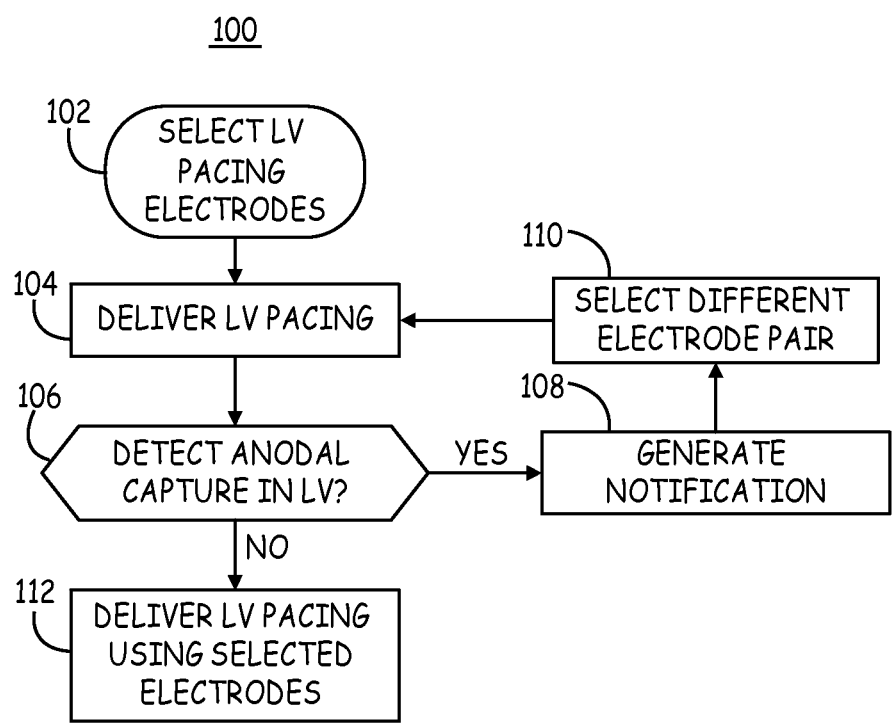
FIG. 3 is a flow chart of a method for selecting electrodes for delivering a pacing therapy.

FIG. 3 is a flow chart of a method for selecting electrodes for delivering a pacing therapy based at least in part on the detection of anodal capture. Flow chart 100 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing circuitry to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102, a bipolar pair of pacing electrodes is selected for delivering a cardiac pacing in a heart chamber. Detection of anodal capture is described herein with regard to detecting anodal capture in the left ventricle during bipolar pacing of the left ventricle. It is recognized that detection of anodal capture during bipolar pacing in another heart chamber, or in another body location, may be performed using the methods described herein. In the illustrative embodiment, a bipolar pair of electrodes is selected from a multi-polar LV CS lead such as lead 18 shown in FIG. 1. LV pacing is delivered at block 104 according to a capture analysis algorithm to detect whether anodal capture is occurring in the LV at block 106. The LV pacing at block 104 may involve both unipolar and bipolar pacing in the LV for making various measurements for detecting anodal capture during bipolar pacing.

If anodal capture is detected, a notification may be generated to a clinician at block 108. The clinician, made aware that anodal capture is occurring, may program the IMD to use a different pacing electrode pair for pacing in the LV.

Additionally or alternatively, a different LV pacing bipole may be selected automatically at block 110. For example, a different electrode may be selected as an anode with the same cathode, located at a desired LV pacing site, in an attempt to obtain cathodal stimulation at the desired pacing site. A different anode selected at block 110 may be within the LV or in another heart chamber, for example, an RV electrode, or the housing of the IMD in order to minimize the likelihood of anodal capture in the LV. Selection of a different electrode pair may involve selecting a different anode only, a different cathode only, or a different anode and a different cathode to achieve cathodal capture at a desired pacing site. If anodal capture is not detected at block 106, LV pacing can be delivered using the selected electrode pair at block 112.

Figure 4A:
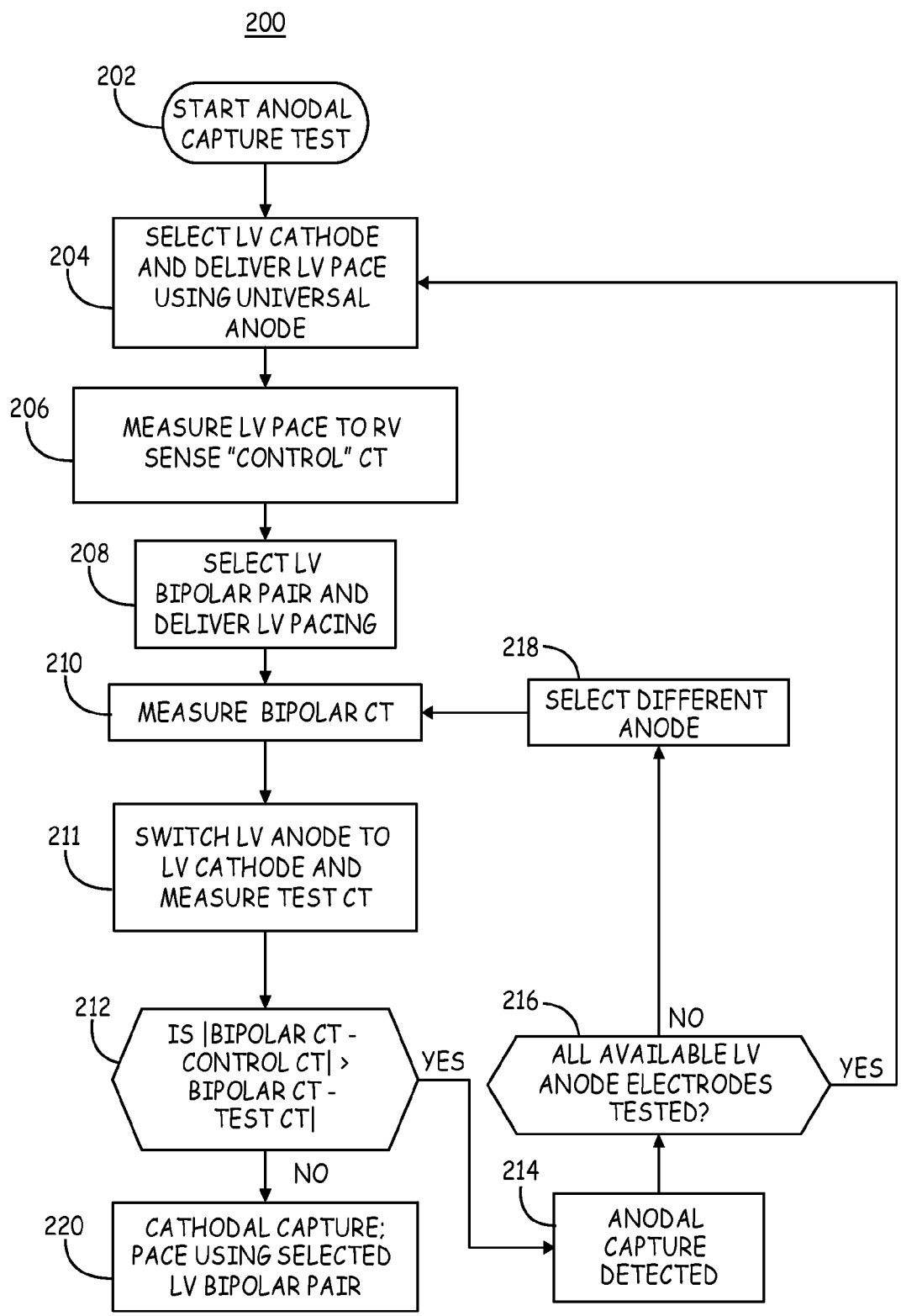
FIG. 4A is a flow chart of a method for detecting anodal capture in the left ventricle according to one embodiment.

FIG. 4A is a flow chart 200 of one method for detecting anodal capture in the LV. At block 202, an anodal capture test is initiated. The anodal capture test may be performed upon command or automatically and may be performed alone or in combination with a capture threshold test. The anodal capture test may be performed automatically on a periodic basis or in response to detecting a change in a physiological signal, e.g. a worsening hemodynamic signal.

At block 204, an LV pacing cathode is selected and LV pacing is delivered between the LV cathode electrode and a "universal" anode. The LV pacing cathode is a candidate pacing cathode being evaluated for the likelihood of anodal capture if the cathode were to be used for delivering a pacing therapy. The "universal" anode is an anode electrode that will be used to measure both a control and test pacing response during evaluation of a given cathode electrode for the presence of anodal capture. A "universal" anode may be positioned away from the LV, such as an RV ring electrode 22, RV coil electrode 24, SVC coil electrode 26, or an electrode located away from the heart, such as a housing electrode 12 formed along the IMD housing, all shown in FIG. 1.

For any of these anode selections, the pacing delivered at block 204 will be unipolar pacing. As used herein, the term "unipolar pacing" refers to pacing using one electrode positioned in or along the heart chamber to be paced and one electrode positioned away from the heart chamber being paced, either in another heart chamber or away from the heart. In one embodiment, unipolar LV pacing is delivered at block 204 between a selected LV cathode electrode and any available electrode positioned away from the LV, which may be in or along another heart chamber, the SVC, the IMD housing, any subcutaneous location, or other locations that are not in or along the LV.

In another embodiment, the "universal" anode may be another electrode in the heart chamber being paced, i.e. the same chamber as the cathode electrode. Examples measurement configurations that include a "universal" anode located away from the paced chamber and a "universal" anode located in the paced chamber will be described in conjunction with FIGS. 4B and 4C.

In a quadripolar LV lead such as lead 22 shown in FIG. 1, the electrodes 30, 32, 34, and 36 may be referred to as LV1, LV2, LV3 and LV4, respectively, moving from the most distal LV1 electrode 30 to the most proximal LV4 electrode 36. The most proximal LV4 electrode 36 may be positioned along the LV base and may be the most desirable cathode electrode for delivering LV basal pacing.

As such, in one example, the LV4 electrode 36 may be selected at block 204 as a pacing cathode in a unipolar LV pacing vector using any available electrode away from the LV as the anode. For example, during the anodal capture analysis algorithm, pacing is delivered between the LV4 electrode 36

(or other selected LV cathode electrode) and an RV electrode, such as RV coil electrode 24 (FIG. 1), serving as the anode.

The time interval between the pacing pulse and an RV depolarization sensed after the LV pacing pulse is measured at block 206 as a control conduction time (CT). Here, and in other embodiments of anodal capture analysis algorithms presently disclosed, when pacing pulses are being delivered to measure a response to the pacing pulses, the pulses are delivered at time intervals that avoid interference of intrinsic depolarizations with the measured response to a pacing pulse. For example, pacing pulses are delivered at a time interval that is shorter than intrinsic RV depolarization arising from conduction from the atria to avoid intrinsic depolarization signals from interfering with CT measurements in the RV. Additionally, premature ventricular contraction (PVC) detection may be employed to avoid measuring a conducted PVC as a conducted depolarization response to the LV pacing pulse. Methods for controlling the timing of test pulses during a capture analysis algorithm and for dealing with the occurrence of PVCs may correspond generally to methods disclosed in U.S. Patent Publication No. 2010/0137935 (Parikh, et al.), hereby incorporated herein by reference in its entirety.

In practice, the pacing pulse amplitude delivered at block 204 may be set to a value just above the capture threshold. The conduction time of a pacing-evoked depolarization from the LV to the RV can decrease with higher pacing voltage. To provide comparable CT intervals measured using different electrode vectors, a consistent pacing pulse amplitude and pulse width relative to a measured capture threshold for a given pacing vector may be used when measuring an LVpace to RVsense CT. For example, a fixed increment above the capture threshold such as about 0.5 V greater than a measured capture threshold, may be used.

The RV EGM signal used for sensing an RV depolarization conducted from the LV may be sensed using the RV tip and ring electrodes 20 and 22. In this embodiment, it is assumed that cathodal capture is occurring in the LV and anodal capture is not occurring at the "universal" anode when the control CT is measured. For example, for an LV-RVcoil pacing configuration used for measuring a control response to an LV pacing pulse, capture is occurring in the LV and is not occurring at the RV coil.

Measuring the relative time of a conducted depolarization (R-wave) relative to an LV pacing pulse may involve measuring the time to an R-wave sense amplifier output. Sensing an R-wave in the RV may be performed using a sense amplifier and auto-adjusting threshold as generally described in U.S. Pat. No. 5,117,824 (Keimel, et al.), hereby incorporated herein by reference in its entirety. In an alternative embodiment, measuring the CT of the conducted RV depolarization relative to an LV pacing pulse may involve analog-to-digital conversion of an ventricular EGM signal and analysis of the digitized EGM signal to determine a local activation time at a sensing bipole located a distance from the pacing cathode. The local activation time may be identified as any fiducial point along the R-wave of the EGM signal, such as a maximum, minimum, peak dV/dt, zero-crossing or other signal feature.

At block 208, a bipolar pair is selected in the LV using the same LV cathode electrode as used to measure the control CT. Any other available LV electrode is selected as the anode in a candidate bipolar pacing vector for use during subsequent therapy delivery. Bipolar LV pacing is delivered using the selected LV cathode and anode. The CT between the LV pacing pulse and a conducted depolarization is measured at block 210 as the bipolar CT. The bipolar LV pacing pulse is delivered just above the capture threshold, for example, a consistent fixed increment above the capture threshold, to provide comparable time interval measurements between pacing vectors with minimized influence of the pacing pulse amplitude on the measured conduction times. It is noted that, while it is known that some type of capture is occurring at the capture threshold, it remains unknown whether that capture is occurring at the anode, cathode, or a combination of both.

At block 211, the polarity of the LV anode used during bipolar LV pacing is switched to a cathode and then used to deliver LV pacing with the same "universal" anode electrode used during measurement of the control CT. A test CT is measured at block 211 to obtain a CT corresponding to capture at the candidate bipolar LV anode site. This test CT measured during LV pacing at the candidate bipolar anode site, i.e. using the candidate bipolar anode as a cathode during pacing with the "universal" anode, gives an estimate of the CT that would be expected if anodal capture is occurring during LV bipolar pacing using the candidate LV bipole.

At block 212, the bipolar CT is compared to the control CT and the test CT to determine if the bipolar CT approximately matches the control CT. If cathodal capture is occurring during pacing with the candidate bipole, the bipolar CT should approximately match the control CT. If anodal is capture is occurring during pacing with the candidate bipole, the bipolar CT should approximately match the test CT. As such, in one embodiment the absolute difference between the candidate bipolar CT and the control CT is compared to the absolute difference between the candidate bipolar CT and the test CT. If the absolute difference between the candidate bipolar CT and the control CT is less than the absolute difference between the candidate bipolar CT and the test CT (a negative result at block 212), the candidate cathode being evaluated (LV4 in the above example) is capturing.

If the bipolar CT is closer to the test CT than the control CT, the anode LV1 in this example is likely capturing. In an alternative embodiment, the test CT may not be measured if the bipolar CT closely matches the control CT within a predefined range, e.g. within approximately 10 ms of the control CT. In some cases, if the LV bipole electrodes are very close together, the conduction times from cathodal and anodal stimulation may not be separable. However, in this case, the impact of pacing from the anode vs. pacing from the cathode during bipolar pacing may have no clinical impact and therefore such discrimination may be unnecessary.

If cathodal capture is occurring, the bipolar CT will be closer to the control CT as determined at decision block 212. Cathodal capture is detected at block 220. The selected candidate LV bipole can be used to deliver LV pacing pulses according to a programmed pacing therapy at block 220. If the candidate bipolar CT is not closer to or does not approximately match the control CT, anodal capture is detected at block 214. A notification of anodal capture may be generated at block 214, and/or a different LV bipolar pair may be selected for evaluation by proceeding to block 216.

If other LV electrodes are available for use as an anode, as determined at block 216, a new candidate bipolar pair using the same cathode and a different anode may be selected at block 218. A bipolar CT is measured again at block 210 using the same LV cathode electrode with a newly selected LV anode electrode and the process continues to block 211.

If all available LV electrodes have been tested as an anode paired with the currently selected LV cathode and resulted in anodal capture detection, the process may return to block 204 to select a different LV electrode as a new candidate cathode and repeat the anodal capture test until a suitable LV bipolar pair is identified that does not result in anodal capture. This process of selecting new candidate bipolar electrode pairs for testing may be a fully automated process or may be semi-automated in which a user responds to a warning of anodal capture detection and selects what actions will be taken next, for example, accept the electrode configuration, select a new anode, select a new cathode, select a new anode and new cathode, perform additional measurements or the like.

In some instances, the control CT and the test CT may be equal. In this situation, a different distant bipole may be selected for sensing a conducted depolarization for measuring the CTs in an attempt to obtain distinct control and test CTs. Alternatively, a different method for discriminating between anodal and cathodal capture may be selected, such as using a different measured response to the pacing pulse, for example evoked response timing or morphology as described below. In another embodiment, if the control and test CTs are equal, the algorithm may be stopped, and an inconclusive test may be reported.

Figure 4B:
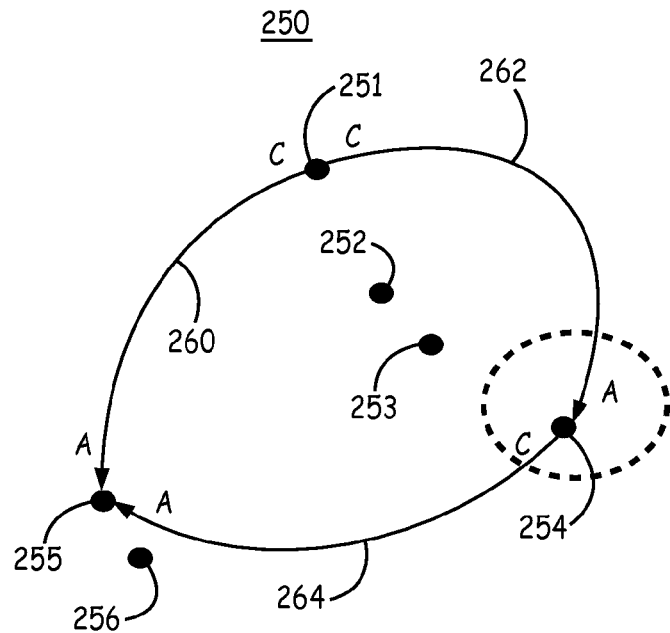
FIG. 4B is a schematic drawing depicting one configuration for making measurements during an anodal capture analysis algorithm.

FIG. 4B is a schematic drawing depicting one configuration 250 for making measurements during an anodal capture test algorithm. In the schematic drawing, electrodes 251, 252, 253, and 254 are positioned along or in a cardiac chamber to be paced, e.g. along the LV. It is recognized that during therapy delivery, pacing may be delivered in one or more heart chambers, not just the chamber being paced during the anodal capture analysis. Electrodes 255 and 256 are positioned away from the paced chamber, e.g. in the RV. Electrode 255, which may be a ring or coil electrode, is shown to be used as a universal anode with any of electrodes 251 through 254 during unipolar pacing. In an illustrative example according to the method described in conjunction with FIG. 4A, a control measurement is made during unipolar pacing between electrode 251 (candidate cathode) and electrode 255 (universal anode), along pacing vector 260 (with the cathodal to anodal polarities indicated by the respective letters "C" and "A").

A control measurement made during this unipolar pacing may be the CT from the pacing cathode 251 to an R-wave sensed at a local site using bipolar sensing electrodes in another heart chamber, such as electrodes 256 and 255 which may correspond to RV tip and ring electrodes. Any bipole located a distance away from the cathode electrode can be used to measure a control CT.

A bipolar measurement is made during bipolar pacing between electrode 251 (candidate cathode) and electrode 254 (anode) along vector 262. With continued reference to the example given above, a bipolar CT may be measured by sensing a local R-wave at the bipole formed by electrodes 255 and 256. If cathodal capture is occurring at candidate cathode 251, the control CT and the bipolar CT are expected to be similar because the conduction time of an evoked response occurring at electrode 251 to the distant bipole electrodes 255 and 256 should be similar in both cases.

The anode electrode 254 of the pacing bipole is switched to a cathode polarity, as indicated by the "C" and "A" notations, to measure a test response during unipolar pacing between electrode 254 (now a cathode) and the universal anode 255 along vector 264. Notice the reversed polarity annotation for electrode 254 from A along vector 262 to C along vector 264 highlighted by dashed circle. The cathode (C) and anode (A) polarities are indicated along vector 264. A test CT is measured at the distant bipolar sensing electrodes 255 and 256. When the bipolar CT measured during pacing along vector 262 more closely matches the test CT measured during pacing along vector 264 than the control measurement made during pacing along vector 260, anodal capture at electrode 254 during bipolar pacing is detected or suspected.

The measured response to a pacing pulse during the anodal capture test may be a CT between the paced heart chamber and another heart chamber as measured by determining the relative time of a locally sensed R-wave (or P-wave if pacing and sensing in the atria) and the preceding pacing pulse. The measurement of a response to a pacing pulse may include other measurements such as a capture threshold measurement, a measurement relating to an evoked response detected in the paced chamber, or any combination thereof, examples of which will be further described below.

Figure 4C:
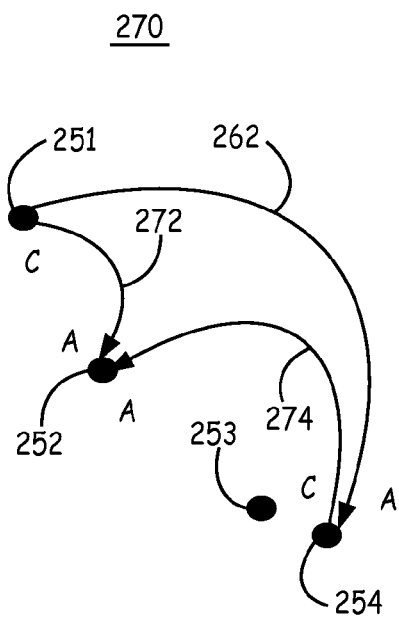
FIG. 4C is a schematic drawing depicting another configuration for making measurements during an anodal capture analysis algorithm.

In FIG. 4C, another configuration 270 for measuring pacing responses for anodal capture detection is depicted schematically. The electrodes 251, 252, 253 and 254 are electrodes positioned in the heart chamber to be paced, such as the LV, during the anodal capture analysis algorithm. In this case, electrodes in the chamber being paced are the only electrodes used during the anodal capture analysis test. This method can be performed, for example in a single-chamber pacing application.

A bipolar measurement is made during pacing along a desired bipolar pacing vector 262 between electrode 251 (candidate cathode) and electrode 254 (anode). A control measurement may be made in this case during pacing along another bipolar vector 272 between electrode 251 (candidate cathode) and another electrode 252 (universal anode) in the same heart chamber. A test measurement is made during pacing along vector 274. The anode electrode 254 used during the bipolar measurement is switched to a cathode electrode, and pacing is delivered using the same universal anode electrode 252 as the control measurement. In other words, anode electrode 252 is used as a universal anode for all control and test measurements made when evaluating a particular candidate cathode electrode 251. This universal anode 252 replaces the need for an anode (e.g. anode 255 in FIG. 4B) positioned away from the chamber being paced during anode capture analysis.

If the response to the pacing pulses is measured as a CT, the CT is measured by determining the relative time from the delivered pacing pulse and a locally sensed R-wave at a sensing bipole in the chamber being paced. In the example shown, electrodes 252 and 253 may be utilized as a sensing bipole for sensing a local R-wave and determining a CT. A sensing bipole may alternatively be an independent pair of electrodes located anywhere along the paced chamber. If the bipolar CT measured during pacing along vector 262 is closer to the test CT (meausured during pacing along vector 274 with electrode 254 as the cathode) than the control CT measured during pacing along vector 272, anodal capture is detected or suspected. The conducted R-wave is expected to arrive at the sensing electrodes 252 and 253 at approximately the same time if cathodal capture is occurring at electrode 251 during pacing along vectors 262 and 272. If not, and particularly if the test CT is closer to the control CT, capture is likely happening at anode 254 during bipolar pacing along vector 262.

Figure 5:
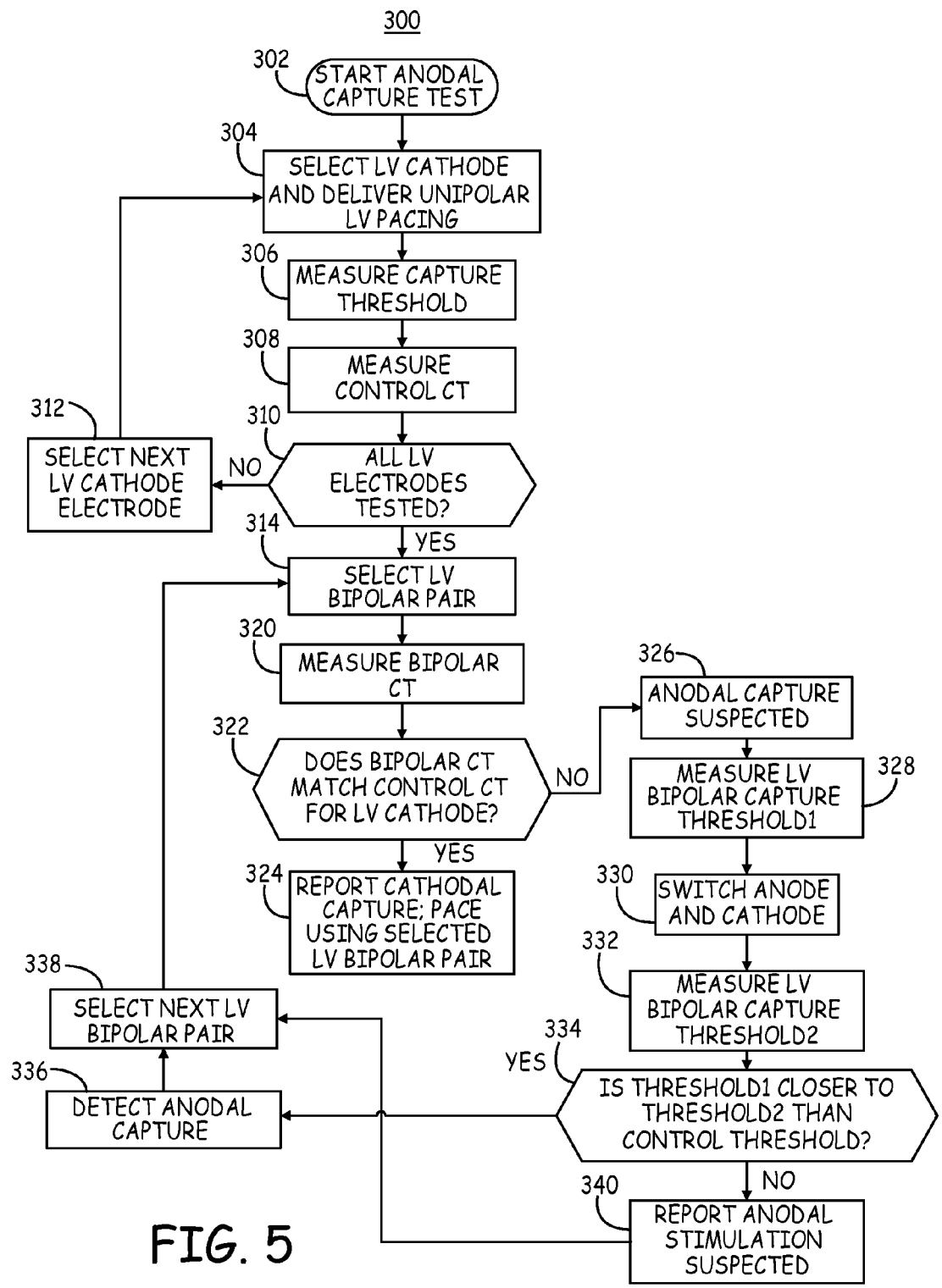
FIG. 5 is a flow chart of a method for detecting anodal capture according to an alternative embodiment.

FIG. 5 is a flow chart 300 of a method for detecting anodal capture according to an alternative embodiment. At block 302, an anodal capture test is initiated. An LV cathode electrode is selected at block 304, and LV pacing is delivered using the candidate LV cathode electrode and a universal anode electrode, which may be located away from the LV, such as the RV coil electrode, such that the pacing is delivered in a unipolar manner. At block 306, the capture threshold for the selected LV cathode and anode is determined. The pacing pulse amplitude is varied until the capture threshold is identified according to a capture threshold test. A capture threshold test is generally described in U.S. Pat. No. 5,873,898

(Hemming, et al.), hereby incorporated herein by reference in its entirety, however other capture threshold measurement methods may be implemented.

The control CT is measured at block 308 as described previously. This process of measuring a capture threshold and a control CT is repeated for all available LV electrodes evaluated as candidate LV cathodes paired one at a time with a universal anode positioned away from the LV as indicated by blocks 310 and 312. The capture threshold data for each candidate LV electrode used as a cathode with an anode located outside the LV is stored in memory along with the corresponding control CT. This "control" data associated with LV cathodal capture during unipolar LV pacing is used in detecting LV anodal capture during LV bipolar pacing using the candidate LV cathodes and various LV anodes.

At block 314, an LV bipolar pair is selected for delivering LV pacing. In one embodiment, a candidate LV bipole is selected based on a desired pacing site during therapy delivery and/or the lowest capture threshold measured at block 306. During LV bipolar pacing only (i.e., no pacing in the RV), the bipolar CT is measured at block 320. The bipolar CT is measured during bipolar pacing using the candidate bipole at the same distant sensing bipole as used to measure the control CT.

The bipolar CT is compared to the control CT at block 322. An approximate match detected at block 322 may be defined as a bipolar CT that is closer to the control CT than to a test CT. The test CT is measured previously at block 304 during cathodal pacing at the candidate bipole anode site. A comparison of the absolute differences between the bipolar CT and control CT and the bipolar CT and the test CT as described previously may be used at block 322 to determine an approximate match between the bipolar CT and the control CT.

If the bipolar CT approximately matches or is closer to the control CT than the test CT, cathodal capture is presumed. Anodal capture is not detected. Cathodal capture may be reported at block 324, and/or LV pacing is delivered at block 324 using the selected LV bipole.

If the bipolar CT does not approximately match the control CT, anodal capture is suspected as indicated at block 326. The measured bipolar CT may be substantially longer or shorter than the control CT.

To determine if anodal capture is occurring, an additional response to the bipolar pacing is measured and compared to a control and/or test response to LV pacing, where the control response uses the candidate cathode and a "universal" anode and the test response using the anode of the candidate bipolar pair switched to a cathode polarity. In the embodiment of FIG. 5, the additionally measured response is the capture threshold.

A capture threshold measurement is performed at block 328 to determine the capture threshold for the candidate LV bipole. The bipolar capture threshold is referred to as threshold1. If the LV cathode of the candidate LV bipolar pair is capturing, the bipolar capture threshold is expected to be similar to the control capture threshold, when the cathode is used with a "universal" anode, such as the RV coil.

The cathode and anode polarity of the selected electrode pair is switched at block 330, and a second LV bipolar capture threshold, referred to as threshold2, is measured at block 332, for this opposite polarity of the candidate LV bipole electrodes. This switched polarity capture threshold provides a "test" response because it provides an expected capture threshold when capture is occurring at the anode of the candidate bipolar pair.

Threshold1 is compared to the control capture threshold and the test capture threshold (theshold2) at block 334. If the LV capture threshold1 is closer to the test threshold2 than it is to the control capture threshold, anodal capture is detected at block 336. A different candidate LV bipolar pair is selected at block 338, and the process returns to block 314 to determine if anodal capture occurs with the new bipolar pair.

If threshold 1 for the candidate bipolar pair is closer to the control threshold, this evidence does not fully support the detection of anodal capture based on measured CTs. Anodal capture may be reported as suspected but not confirmed at block 340. A clinician may choose to accept the candidate bipolar pair for therapy delivery, or another candidate bipolar pair is selected at block 338.

In Table I, example capture threshold test results are listed for LV pacing electrode pairs. The control capture threshold is listed for each LV electrode, LV1, LV2, LV3 and LV4, available on a quadripolar CS LV lead used as a cathode paired with an RV coil electrode as a "universal" anode for collecting control data. Note that the capture threshold for LV4-RVcoil is 8.1 V, considerably greater than the capture threshold for any of the other LV electrodes selected as cathodes.

The bipolar capture thresholds for each bipolar combination including LV4 as the cathode (and LV1, LV2, or LV3 selected as the anode) is also listed. Note that the bipolar capture threshold for LV4 to LV1 pacing is low, 1.0 V. This capture threshold would be measured as the bipolar threshold1 at block 328 when LV4 is selected as the candidate cathode.

The capture threshold for LV1 to LV4 is 0.8 V. This capture threshold would be measured as the test threshold2 at block 332, for the reversed polarity of the candidate LV bipole. The capture threshold1 (LV4 to LV1) is much less than the control capture threshold (LV4 to LVcoil), and is nearer test threshold2 (LV1-LV4). This result suggests that capture is not occurring at LV4, which was associated with a high capture threshold when paired with the RV coil electrode. Instead, anodal capture is probably occurring at LV1 when the LV4-LV1 bipole is selected.

TABLE I

Capture thresholds measured during LV pacing.

| Pacing vector | Capture Threshold (V) |
|---|---|
| LV1 to RV coil | 0.6 |
| LV2 to RV coil | 1.1 |
| LV3 to RV coil | 2.0 |
| LV4 to RV coil | 8.1 |
| LV1 to LV2 | 0.7 |
| LV1 to LV3 | 0.8 |
| LV1 to LV4 | 0.8 |
| LV4 to LV1 | 1.0 |
| LV4 to LV2 | 4.7 |
| LV4 to LV3 | 9.2 |

Anodal capture thresholds will typically be significantly higher than cathodal capture thresholds. However, even if the threshold1 is not much less than the control capture threshold or is closer to the control threshold than the test threshold 2, anodal capture may still be occurring when the bipolar CT is much shorter than the control CT. For example simultaneous anodal and cathodal capture may be occurring when the bipolar CT does not approximately match the control CT but the capture threshold data does not provide strong evidence for anodal capture. Suspected anodal stimulation, in such cases, can be reported at block 340. A clinician may decide whether to select a different electrode pair at block 338 or accept the tested bipole. In some cases, simultaneous anodal and cathodal capture may be acceptable, for example based on an analysis hemodynamic parameters.

Figure 6:
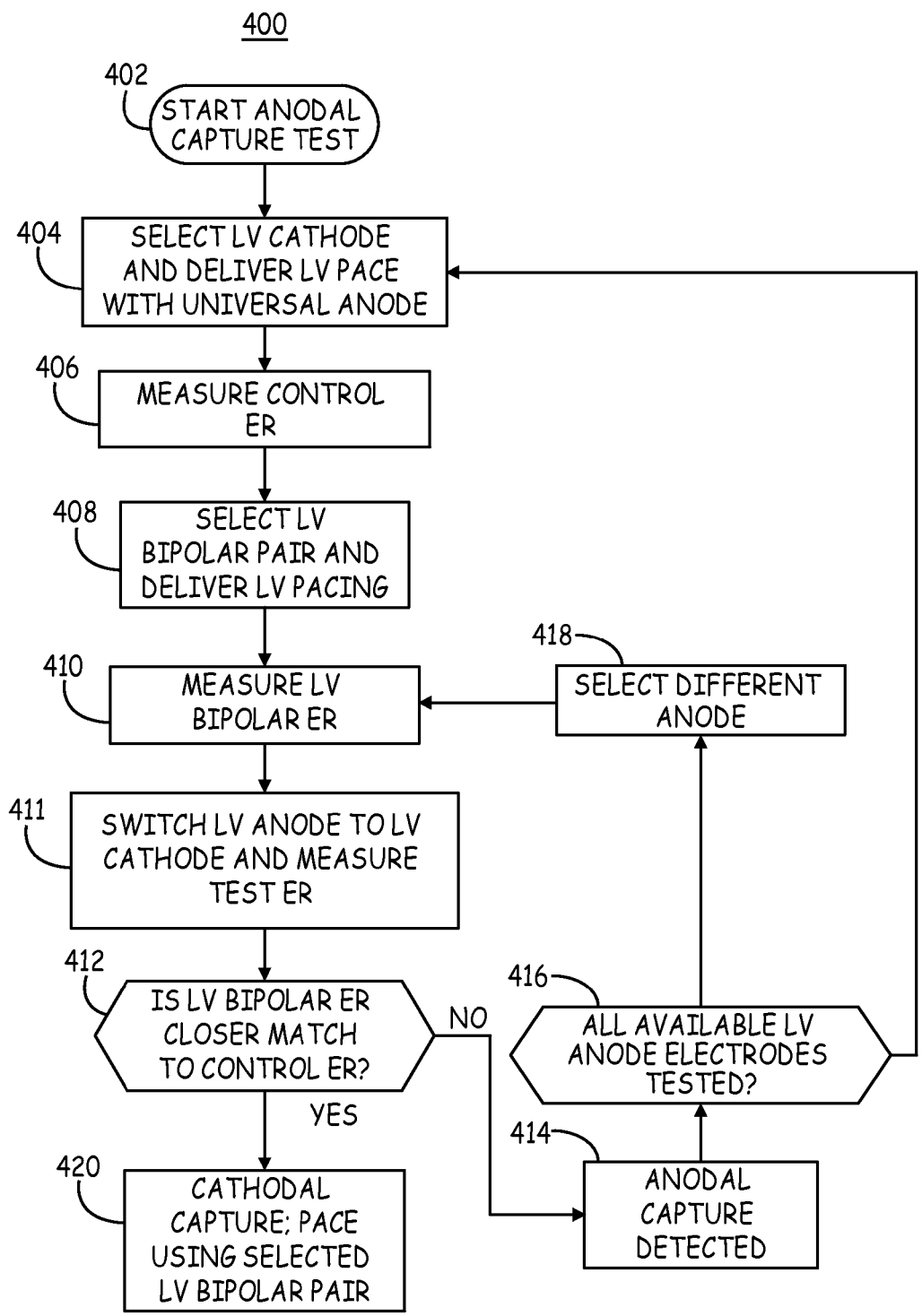
FIG. 6 is a flow chart of a method for discriminating between anodal and cathodal capture according to yet another embodiment.

FIG. 6 is a flow chart 400 of a method for discriminating between anodal and cathodal capture according to yet another alternative embodiment. An anodal capture test is initiated at block 402. An electrode positioned along or in the LV is selected as a candidate cathode at block 404 and used to deliver LV pacing pulses with a universal anode, which may positioned away from the LV or along the LV as described above in conjunction with FIGS. 4B and 4C. In one embodiment, the universal anode is a large electrode positioned away from the LV, such as a housing electrode along the IMD housing or an RV coil electrode.

At block 406, a control LV evoked response (ER) measurement is made. The control ER signal is measured from an EGM signal obtained at the pacing cathode electrode and another sensing electrode. An ER measurement may relate to a time interval from the pacing pulse to a point along the ER signal, a measurement of a morphological feature of the ER signal, or a template of the morphology of the ER signal waveform. ER sensing is generally disclosed in U.S. Pat. No. 7,123,963 (Sawchuk et al.), hereby incorporated herein by reference in its entirety. The ER signal is digitized and digital analysis of the waveform is performed to obtain a time interval or morphology-related measurement. An ER morphology measurement may be made using any waveform analysis method. A wavelet morphology analysis method that may be implemented to perform an ER morphology measurement at block 406 is generally described in U.S. Pat. No. 6,393,316 (Gillberg, et al.), hereby incorporated herein by reference in its entirety. The control ER measurement is stored at block 406 for future comparison for discriminating anodal and cathodal capture.

At block 408, an LV bipolar pacing pair is selected using the candidate LV cathode electrode and any available LV anode. Bipolar LV pacing is delivered using the selected bipole. At block 410, the ER measurement is repeated during the LV bipolar pacing. At block 411, the LV anode used during bipolar pacing is switched to a cathode and LV pacing is delivered using the "universal" anode that was also used for measuring the control ER. A test ER measurement is performed when the candidate bipole anode is switched to a cathode to obtain a test ER measurement corresponding to capture occurring at the anode site of the candidate LV bipole.

At block 412, the bipolar ER measurement is compared to the control ER measurement and the test ER measurement. If the bipolar ER measurement is closer to the control ER measurement, cathodal capture is detected at block 420. The device may be programmed to automatically pace in the LV using the candidate LV bipolar pair.

If the bipolar ER measurement is closer to the test ER measurement, anodal capture is suspected and a warning is generated at block 414. In one embodiment, a morphology matching score is computed between the bipolar ER morphology and the control ER morphology. A second morphology matching score is computed between the bipolar ER morphology and the test ER morphology. If the morphology matching score corresponding to the control ER morphology is higher than the matching score corresponding to the test ER morphology, cathodal capture is detected. If the morphology matching score corresponding to the test ER morphology is higher, anodal capture is detected.

If anodal capture is detected, other available LV electrodes may be selected as anodes with the same candidate LV cathode electrode as indicated at blocks 416 and 418 to identify a bipolar pair that does not result in anodal stimulation. If all available LV anodes have been tested with the candidate cathode, a new candidate cathode may be selected at block 404.

The use of an ER measurement may be used alone or in any combination with one or both of the CT measurements and capture threshold measurements described above for discriminating between anodal and cathodal capture. For example, an ER measurement may be used to confirm the suspected presence of anodal capture based on CT measurements.

Figure 7:
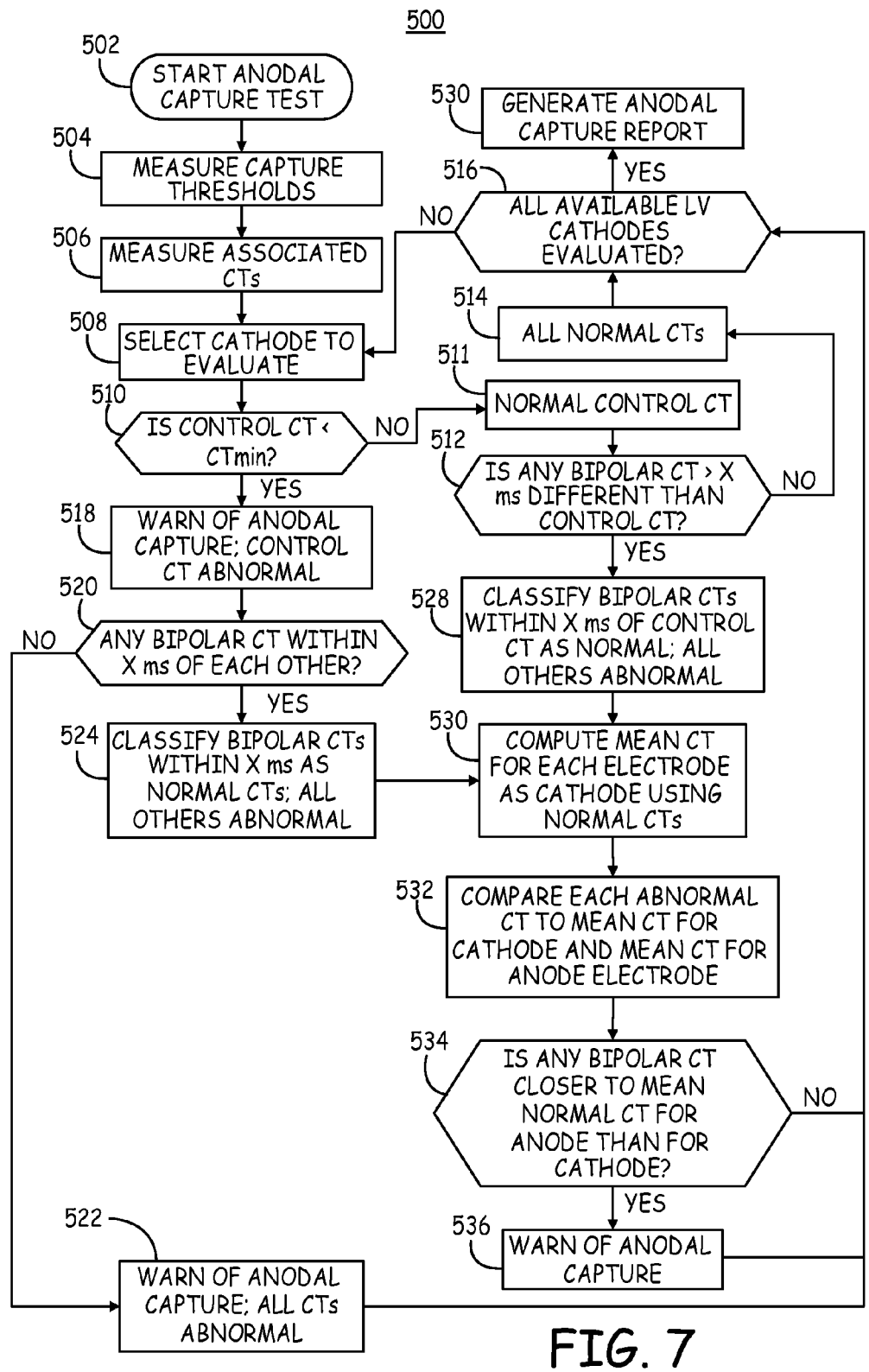
FIG. 7 is a flow chart of a method for performing anodal capture analysis and reporting results according to one embodiment.

FIG. 7 is a flow chart 500 of a method for performing anodal capture analysis and reporting according to one embodiment. In the above-described embodiments, it is assumed that LV pacing delivered to obtain control measurements does not result in anodal capture. In other words it is assumed that anodal capture does not occur at a "universal" anode used to measure control responses and sometimes test responses to pacing pulses. In some cases, anodal capture may be occurring at the universal anode, when located in the same or another heart chamber. This anodal capture will produce confounding results when discriminating between anodal and cathodal capture during bipolar pacing in a heart chamber.

When the universal anode is selected away from the heart, such as a housing electrode along the IMD housing or a subcutaneous large surface area electrode, capture at the universal anode can be avoided. When in the heart, such as the RV, anodal capture without cathodal capture in the LV or a combination of anodal and cathodal capture simultaneously in both the RV and LV could occur. The method shown in flow chart 500 is used to test all available bipole combinations in a heart chamber and discriminate between anodal and cathodal capture, even when a control measurement may represent anodal capture at the universal anode rather than capture at the candidate cathode. A report can be generated indicating under what conditions anodal capture is detected or suspected providing a clinician with valuable information for selecting pacing vectors for achieving a desired therapeutic benefit.

At block 502, an anodal capture test is started. The test may be initiated upon user command, upon implant detection or other triggering event. In some embodiments, the anodal capture evaluation is performed in conjunction with capture threshold testing such that both capture thresholds and any detected or suspected anodal capture may be reported together. As such, at block 504, capture thresholds are measured for each candidate cathode, paired with a universal anode to obtain control capture thresholds and in candidate bipolar pairs with each available anode to obtain bipolar capture thresholds with all possible bipoles.

At block 506, the associated CTs for each pacing combination are measured during the capture threshold tests. For example, during LV pacing, the control CT is measured for each candidate LV cathode paired with the universal anode, e.g. the RV coil electrode. These control CTs are stored for each respective candidate cathode. Additionally, during capture threshold measurements for each candidate bipole, an associated bipolar CT is measured. Each candidate LV cathode is paired with all available LV anode electrodes one at a time such that all possible bipolar LV pacing vectors are used to deliver bipolar LV pacing and measure a corresponding bipolar CT at a distant sensing site.

At block 508, a candidate cathode is selected for evaluation for potential anodal capture. The control CT measured for the candidate cathode (during pacing with the universal anode) is compared to a minimum expected CT at block 510. A physiological minimum CT is previously established and stored in IMD memory. An established minimum CT and may be based on clinical data or individual patient data as an expected conduction time from the cathode pacing site to a distant bipole sensing a local R-wave. The distant bipole sensing a conducted depolarization signal typically but not necessarily including the universal anode as one of the sensing electrodes. The sensing bipole may be in the paced heart chamber or the opposite heart chamber. In one embodiment, the control CT is measured using a sensing electrode pair in the RV, e.g. RV tip to RV ring. A minimum CT from LV pace to RV sense is defined as approximately 60 ms. If the control CT measured for the candidate cathode paired with a universal anode positioned in the RV is less than the minimum CT, anodal capture is likely to be occurring in the RV because conduction from the LV to the RV is not expected to occur faster than the minimum CT.

If the control CT is not less than a minimum physiological CT (negative result at decision block 510), cathodal capture is likely occurring in the LV during pacing using the universal anode. This result of the control CT being greater than the minimum CT indicates that the control CT is a reliable measure for use in discriminating anodal capture during bipolar pacing. At block 511 the control CT is classified as normal, and at block 512 each bipolar CT measured for the cathode under evaluation is compared to the normal control CT.

If all bipolar CTs measured for the candidate cathode are within a previously established threshold range of the control CT at block 512, all bipolar pacing vectors using the candidate cathode under evaluation are labeled as having normal CTs at block 514. The threshold range used at block 512 may be defined, for example, as approximately 10 ms. The "normal" CTs that are within a threshold range of the control CT are likely to be associated with cathodal capture. If additional candidate cathodes remain to be evaluated, as determined at block 516, the next candidate cathode is selected for evaluation at block 508.

Returning to block 512, if any bipolar CT is outside a threshold range of the control CT, that bipolar CT is classified as abnormal at block 528. Any bipolar CTs using the candidate cathode that are within the threshold range of the control CT are classified as normal at block 528. As such, for a given cathode electrode, some bipolar CTs may be classified as abnormal and some may be classified as normal depending whether the associated CT falls within a predefined range of the normal control CT.

At block 530, a mean CT is computed for each electrode being tested. A mean CT is computed using only CTs classified as normal for a given cathode. When arriving at block 530 from block 528, the normal CTs include a normal control CT and any bipolar CTs classified as normal at block 528.

At block 532, a bipolar CT classified as abnormal is compared to the mean CT for the candidate cathode and to the mean CT computed for the electrode used as an anode in the candidate bipole, when the abnormal bipolar CT was measured. The mean CT computed for the anode associated with an abnormal CT is computed from all bipolar and control CTs measured for the anode, which switched to a cathode polarity, and classified as normal CTs. If an abnormal bipolar CT is closer to the mean CT computed for the candidate bipole anode, as determined at block 534, a warning of anodal capture for the associated bipole is generated at block 536. If all of the abnormal CTs are closer to the mean CT computed for the candidate cathode, then no warning of anodal capture is generated. The process advances to block 516.

Returning to block 510, if a control CT is less than the minimum CT, a warning of anodal capture is generated at block 518 for the candidate cathode and universal anode pair. The control CT is classified as abnormal for the candidate cathode under evaluation. In this case, the control CT is not deemed reliable for discriminating between anodal and cathodal capture during bipolar pacing.

In this situation, each bipolar CT measured for the candidate cathode is compared to each of the other bipolar CTs measured for that cathode at block 520. If none are within a previously established range of each other, for example, within approximately 10 ms of each other, the all of the bipolar CTs measured for the candidate cathode being evaluated are labeled "abnormal" at block 522. A warning of anodal capture using the candidate cathode is generated. The process proceeds to block 516 to evaluate the next candidate cathode.

If any bipolar CTs are within a predefined range of another bipolar CT for the same candidate cathode as determined at decision block 520, all bipolar CTs within a threshold range of another bipolar CT are classified as normal at block 524. All "outliers" that are not within an established threshold range of at least one other bipolar CT are classified as abnormal CTs at block 524.

At block 530, a mean CT is computed for each electrode using all normal CTs measured for the given electrode. When arriving at block 530 from block 524, the control CT is excluded from computing a mean CT for the candidate cathode because the control CT has been classified as abnormal. All bipolar CTs falling within an established range of at least one other bipolar CT and therefore classified as normal are used to compute the mean CT for a given electrode.

Any bipolar CTs classified as abnormal for the candidate cathode are compared to the mean CT for the candidate cathode at block 532. An abnormal bipolar CT is additionally compared to a mean CT computed for the electrode being used as the anode in the candidate bipole resulting in the abnormal CT. If an abnormal bipolar CT is closer to the mean CT determined for the electrode now being used as an anode, anodal capture is likely occurring. If the abnormal CT is closer to the mean CT determined for the candidate cathode, cathodal capture is likely to be occurring. In this way, if the cathode being evaluated results in cathodal capture for some lead vectors, these can be identified as bipolar vectors having close CT measurements, whereas outliers can be identified as "abnormal" and separated from normal bipolar CT measurements, even when the control CT measurement is classified as abnormal.

If there are any bipolar CT measurements that are closer to the mean CT for the anode electrode than to the mean CT for the cathode electrode as determined at decision block 534, then a warning of anodal capture for the associated bipole(s) is generated at block 536. If all abnormal CTs are closer to the mean CT computed for the candidate cathode than the mean CT for the associated anode, no warning of anodal capture is generated. The process returns to block 516. In this way, anodal capture is detected and discriminated from cathodal capture during bipolar pacing even when a control response using a universal anode results in suspected anodal capture.

After evaluating all candidate cathodes, an anodal capture report is generated at block 530. The report may be an on-screen display, printable report or other format including text, tables, or graphs of data determined during the anodal capture test. The anodal capture report may additionally include capture threshold data and/or evoked response measurement data. The anodal capture report will warn of anodal capture for any cathode found to have all abnormal CTs associated with every possible bipolar pacing pair tested. The report may further warn of possible anodal capture for any specific bipolar vectors found to have abnormal CTs closer to a mean CT computed for the anode of the bipolar vector than to a mean CT computed for the cathode of the bipolar vector. Any candidate cathode having all normal CTs for every bipolar vector tested may be indicated as a recommended cathode for therapy delivery and avoidance of anodal capture.

Figure 8:
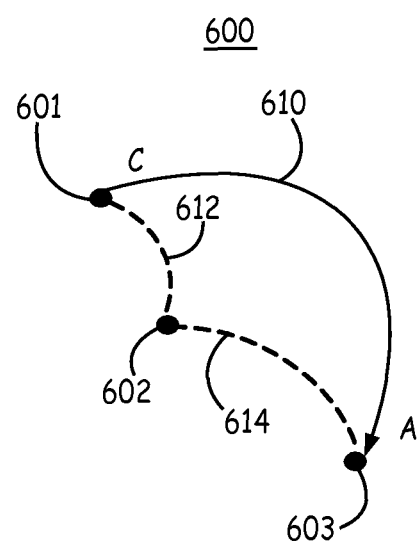
FIG. 8 is a schematic diagram of a configuration for detecting anodal capture during bipolar pacing using evoked response sensing.

FIG. 8 is a schematic diagram of a configuration 600 for detecting anodal capture during bipolar pacing using evoked response sensing. Bipolar pacing is delivered along a vector 610 between a candidate cathode electrode 601 and candidate anode electrode 603. ER sensing is performed at both the cathode 601 and the anode 603 using a third indifferent electrode 602. In other embodiments, ER sensing performed at the cathode 601 and at the anode 603 may use separate indifferent electrodes for sensing the local ER at the respective electrode 601 or 603, rather than a shared indifferent electrode as shown here.

Figure 9:
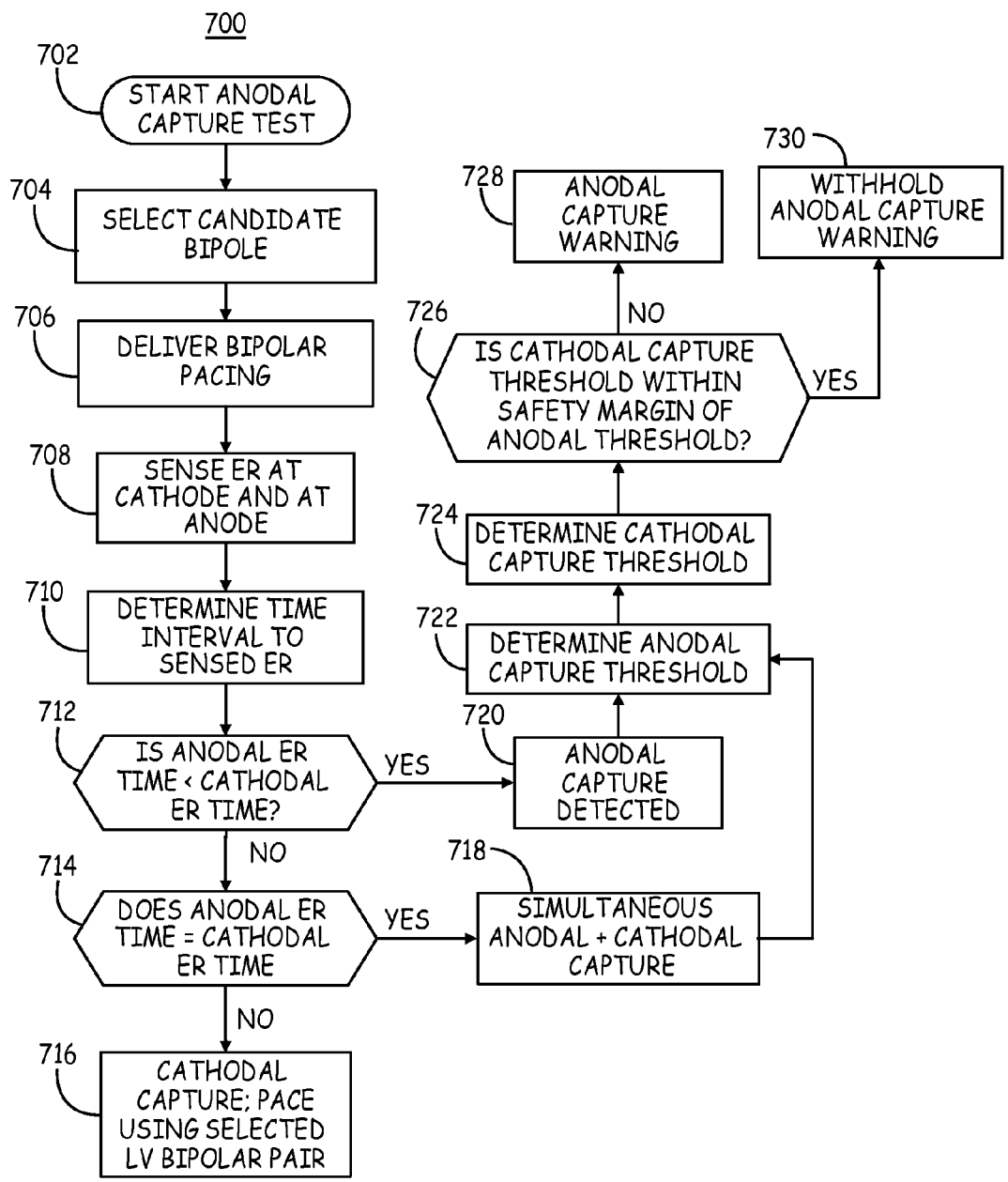
FIG. 9 is a flow chart of a method for detecting anodal capture during bipolar pacing using evoked response sensing at both the candidate cathode and anode as generally depicted in the configuration of FIG. 8.

FIG. 9 is a flow chart 700 of a method for detecting anodal capture during bipolar pacing using ER sensing at both the candidate cathode and anode as generally depicted in the configuration of FIG. 8. At 702, the anodal capture test is initiated. A candidate bipole is selected at block 704, and bipolar pacing is delivered at block 706. An ER is sensed at both the cathode electrode and the anode electrode at block 708. A time interval to the ER signals is determined at block 710. The timing of the evoked responses relative to a delivered pacing pulse can be the timing of a sense amplifier output or the timing of a feature in the digitized EGM signal, such as the maximum amplitude or slope or other features listed previously.

At block 712, the anodal ER time is compared to the cathodal ER time. If an ER is sensed at the anode earlier than at the cathode, anodal capture is detected at block 720. If the ER signals are sensed substantially simultaneously, as determined at block 714, simultaneous anodal and cathodal capture is detected at block 718.

If the ER is sensed earlier at the cathode than at the anode, cathodal capture is detected at block 716. Anodal capture is not detected. The candidate bipole may be selected as a bipolar pacing pair for therapy delivery.

If simultaneous anodal and cathodal capture is detected and/or if anodal capture is detected, the anodal and cathodal capture thresholds may be determined at block 722 and 724, respectively. In one embodiment, the pacing pulse amplitude is adjusted until an ER signal within a predetermined time interval of the pacing pulse disappears. The lowest pacing pulse amplitude at which the ER occurs at a given electrode within a predetermined time interval is determined as the capture threshold.

If the cathodal capture threshold is within a narrow range of the anodal capture threshold, such as within a pacing safety margin, as determined at block 726, an anodal capture warning is withheld at block 730. Since pacing will generally occur at a pacing safety margin above a capture threshold, anodal and cathodal capture thresholds falling within a safety margin of each other will generally result in simultaneous anodal and cathodal capture. Simultaneous anodal and cathodal capture may be acceptable in many pacing therapies making an anodal capture warning unnecessary.

If the capture threshold is substantially higher at the cathode than at the anode, anodal stimulation only may occur for a range of pacing pulse amplitudes. An anodal capture warning is generated at block 728 if the cathodal capture threshold is not within a predetermined narrow range, for example within a pacing safety margin, of the anodal capture thresholds as determined at block 726.

Figure 10:
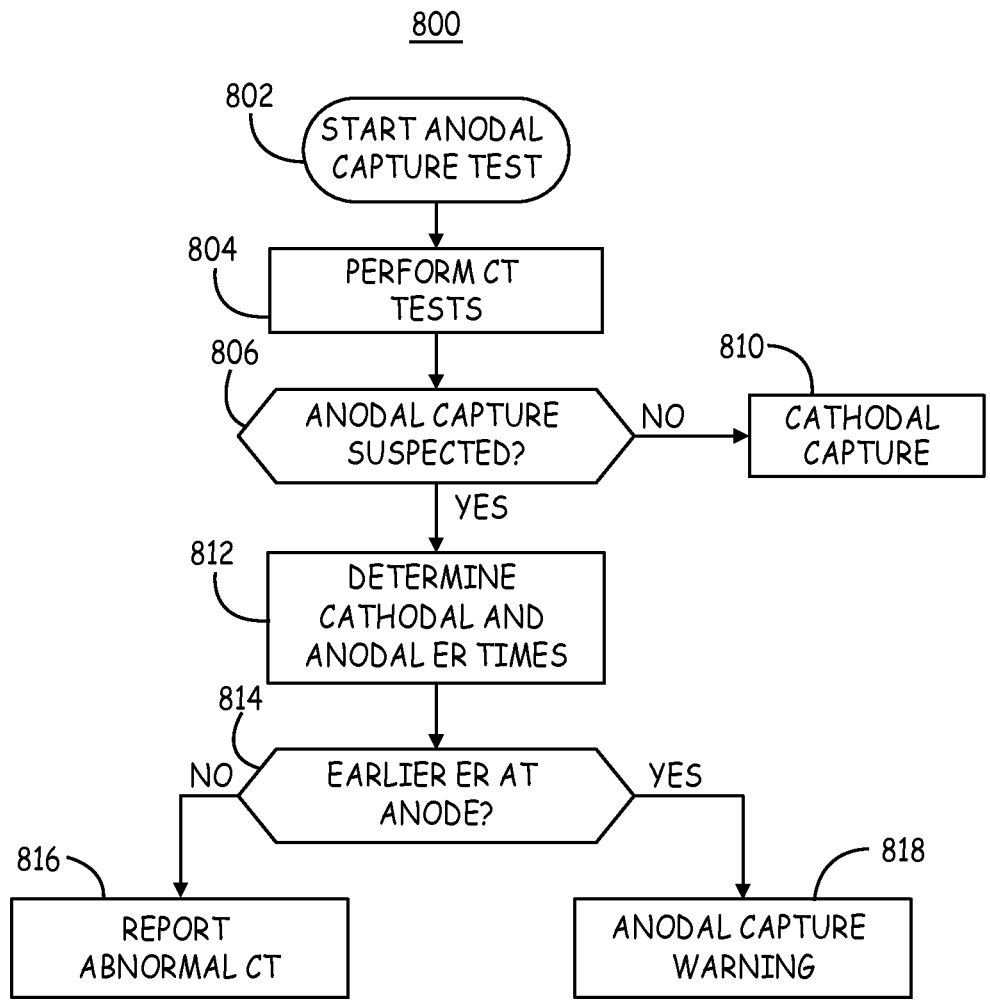
FIG. 10 is a flow chart of a method for detecting and discriminating anodal, cathodal and simultaneous anodal and cathodal capture during bipolar pacing.

FIG. 10 is a flow chart 800 of a method for detecting and discriminating anodal, cathodal and simultaneous anodal and cathodal capture during bipolar pacing. At block 802 the anodal capture test is started for a selected bipole and begins by performing an analysis of CT at block 804 by measuring a control, bipolar and test CT as described previously. If anodal capture is not suspected based on the CT measurements, as determined at decision block 806, cathodal capture is detected at block 810.

If anodal capture is suspected at block 806, the ER is measured at the anode and the cathode of the candidate bipole during bipolar pacing at block 812. If an ER is sensed earlier at the anode than at the cathode, as determined at decision block 814, the suspected anodal capture is confirmed and a warning is generated at block 818. If the ER does not occur earlier at the anode than at the cathode, an abnormal CT may be reported at block 816. The ER measurements do not support anodal capture detection, but an unexpected bipolar CT may be reported to allow a clinician to further evaluate the candidate bipole or alternative pacing bipoles.

In the flow charts presented herein, it is recognized that all blocks shown may not be performed in some embodiments or may be performed in a different order than the order shown. For example, in some embodiments, CT, capture threshold data, and/or ER data, alone or in any combination, may be measured for all available electrode vectors to allow an optimal bipolar pacing vector to be selected. In other embodiments, anodal capture analysis data may be acquired for a desired bipolar vector and if anodal capture is not suspected based on the anodal capture analysis data, the bipolar vector may be selected without further testing. The various measurements described herein for discriminating between anodal and cathodal capture, such as CT measurements, capture threshold measurements, and ER time or morphology measurements may be performed in any combination.

Thus, an apparatus and method for discriminating between anodal and cathodal capture during bipolar pacing have been presented in the foregoing description with reference to specific embodiments. It is appreciated that various modifications to the referenced embodiments may be made without departing from the scope of the disclosure as set forth in the following claims.

The invention claimed is:

1. A method for detecting anodal cardiac capture during bipolar electrical stimulation, the method comprising:
   delivering a first pacing pulse using a first bipole comprising a first cathode and a first anode both positioned along a heart chamber;
   delivering a second pacing pulse using the first cathode and a second anode;
   measuring a first response to the first pacing pulse;
   measuring a second response to the second pacing pulse;
   detecting anodal capture of the heart chamber by the first pacing pulse at the first anode in response to a first difference between the first response and the second response;
   switching the polarity of the first anode to a cathode;
   delivering a third pacing pulse between the first anode switched to the cathode polarity and the second anode;
   measuring a third response to the third pacing pulse; and
   detecting anodal capture in response to the first difference being greater than a second difference between the first response and the third response.

2. The method of claim 1, wherein the first bipole is positioned along a heart chamber and delivering the second pacing pulse comprises selecting the second anode as an electrode positioned away from the heart chamber and delivering the second pacing pulse as a unipolar pacing pulse.

3. The method of claim 1, wherein measuring the responses to the first and second pacing pulses respectively comprises measuring a first conduction time between the first pacing pulse and a subsequent depolarization sensed at a sensing electrode positioned a distance from the first bipole and a second conduction time between the second pacing pulse and a subsequent depolarization sensed at the sensing electrode.

4. A method for detecting anodal cardiac capture during bipolar electrical stimulation, the method comprising:
   delivering a first pacing pulse using a first bipole comprising a first cathode and a first anode both positioned along a heart chamber;
   delivering a second pacing pulse using the first cathode and a second anode;
   measuring a first response to the first pacing pulse;
   measuring a second response to the second pacing pulse;
   detecting anodal capture of the heart chamber by the first pacing pulse at the first anode in response to a first difference between the first response and the second response;
      measuring a first capture threshold corresponding to the first bipole;
      measuring a second capture threshold corresponding to the first cathode and the second anode;
      delivering the first pacing pulse at a fixed increment above the first capture threshold and delivering the second pacing pulse at the fixed increment above the second capture threshold, wherein measuring the responses to the first and second pacing pulses respectively comprises measuring a first conduction time between the first pacing pulse and a subsequent depolarization sensed at a sensing electrode positioned a distance from the first bipole and a second conduction time between the second pacing pulse and a subsequent depolarization sensed at the sensing electrode.

5. The method of claim 1 wherein delivering the third pacing pulse comprises selecting the first anode and the second anode from a plurality of electrodes positioned along a single heart chamber.

6. The method of claim 1 wherein the first bipole is positioned along a heart chamber and delivering the second pacing pulse comprises selecting the second anode as an electrode positioned away from the heart chamber.

7. The method of claim 1, wherein measuring the first response to the first pacing pulse further comprises delivering at least one additional pacing pulse to determine a first capture threshold corresponding to the first bipole,
   measuring the second response to the second pacing pulse further comprises delivering at least one additional pacing pulse to determine a second capture threshold corresponding to the first cathode and the second anode,
   wherein detecting anodal capture further comprises determining a first capture threshold difference between the first capture threshold and the second capture threshold.

8. The method of claim 7, further comprising measuring the first capture threshold and the second capture threshold in response to the first difference being greater than a threshold.

9. A method for detecting anodal cardiac capture during bipolar electrical stimulation, the method comprising:
   delivering a first pacing pulse using a first bipole comprising a first cathode and a first anode both positioned along a heart chamber;
   delivering a second pacing pulse using the first cathode and a second anode;
   measuring a first response to the first pacing pulse;
   measuring a second response to the second pacing pulse;
   detecting anodal capture of the heart chamber by the first pacing pulse at the first anode in response to a first difference between the first response and the second response;
      switching the polarity of the first anode to a cathode;
      switching the polarity of the first cathode to an anode; and
      measuring a third capture threshold corresponding to a second bipole comprising the first cathode switched to the anode polarity and the first anode switched to the cathode polarity;
   wherein detecting anodal capture further comprises detecting anodal capture in response to the first capture threshold difference being greater than a second capture threshold difference between the first capture threshold and the third capture threshold, wherein measuring the first response to the first pacing pulse further comprises delivering at least one additional pacing pulse to determine a first capture threshold corresponding to the first bipole, measuring the second response to the second pacing pulse further comprises delivering at least one additional pacing pulse to determine a second capture threshold corresponding to the first cathode and the second anode, and wherein detecting anodal capture further comprises determining a first capture threshold difference between the first capture threshold and the second capture threshold.

10. The method of claim 1, wherein measuring the first response comprises measuring a first evoked response subsequent to the first pacing pulse and measuring the second response comprises measuring a second evoked response subsequent to the second pacing pulse.

11. The method of claim 10, wherein measuring the first and second evoked responses comprises at least one of measuring a time interval from the respective first pacing pulse and the second pacing pulse to the sensed first evoked response and the second evoked response and determining a morphological feature of the first and second evoked responses.

12. A method for detecting anodal cardiac capture during bipolar electrical stimulation, the method comprising:
   delivering a first pacing pulse using a first bipole comprising a first cathode and a first anode both positioned along a heart chamber;
   delivering a second pacing pulse using the first cathode and a second anode;
   measuring a first response to the first pacing pulse;
   measuring a second response to the second pacing pulse;
   detecting anodal capture of the heart chamber by the first pacing pulse at the first anode in response to a first difference between the first response and the second response;
   measuring a time to a first evoked response sensed at the first cathode and measuring a time to a second evoked response sensed at the first anode;
   responsive to the second evoked response occurring earlier than the first evoked response performing a capture threshold test to determine an anodal capture threshold and a cathodal capture threshold;
   establishing a pacing safety margin; and
   generating a warning of anodal capture in response to the cathodal capture threshold being more than the pacing safety margin greater than the anodal capture threshold.

13. A medical device for detecting anodal cardiac capture, comprising:
a plurality of electrodes for sensing cardiac signals and delivering cardiac pacing pulses;
a therapy delivery module for delivering cardiac pacing pulses to a patient's heart via the plurality of electrodes;
cardiac signal sensing circuitry for receiving signals from the plurality of electrodes; and
a controller configured to:
control the therapy delivery module to deliver a first pacing pulse using a first bipole comprising a first cathode and a first anode both positioned along a heart chamber and deliver a second pacing pulse using the first cathode and a second anode;
measure a first response of a received cardiac signal to the first pacing pulse;
measure a second response of the received cardiac signal to the second pacing pulse; and
detect anodal capture of the heart chamber by the first pacing pulse at the first anode in response to a first difference between the first response and the second response, wherein the controller is further configured to:
switch the polarity of the first anode to a cathode;
cause the therapy delivery module to deliver a third pacing pulse between the first anode switched to the cathode polarity and the second anode;
measure a third response to the third pacing pulse; and
detect anodal capture in response to the first difference being greater than a second difference between the first response and the third response.

14. The device of claim 13, wherein the first bipole is positioned along a heart chamber, the controller further configured to cause the therapy delivery module to deliver the second pacing pulse by selecting the second anode as an electrode positioned away from the heart chamber.

15. The device of claim 13, wherein the controller is configured to measure the responses to the first and second pacing pulses respectively by measuring a first conduction time between the first pacing pulse and a subsequent depolarization sensed at a sensing electrode positioned a distance from the first bipole and a second conduction time between the second pacing pulse and a subsequent depolarization sensed at the sensing electrode.

16. A medical device for detecting anodal cardiac capture, comprising:
a plurality of electrodes for sensing cardiac signals and delivering cardiac pacing pulses;
a therapy delivery module for delivering cardiac pacing pulses to a patient's heart via the plurality of electrodes;
cardiac signal sensing circuitry for receiving signals from the plurality of electrodes; and
a controller configured to:
control the therapy delivery module to deliver a first pacing pulse using a first bipole comprising a first cathode and a first anode both positioned along a heart chamber and deliver a second pacing pulse using the first cathode and a second anode;
measure a first response of a received cardiac signal to the first pacing pulse;
measure a second response of the received cardiac signal to the second pacing pulse; and
detect anodal capture of the heart chamber by the first pacing pulse at the first anode in response to a first difference between the first response and the second response, wherein the controller is further configured to:
measure a first capture threshold corresponding to the first bipole;
measure a second capture threshold corresponding to the first cathode and the second anode; and
cause the therapy delivery module to deliver the first pacing pulse at a fixed increment above the first capture threshold and delivering the second pacing pulse at the fixed increment above the second capture threshold, wherein the controller is configured to measure the responses to the first and second pacing pulses respectively by measuring a first conduction time between the first pacing pulse and a subsequent depolarization sensed at a sensing electrode positioned a distance from the first bipole and a second conduction time between the second pacing pulse and a subsequent depolarization sensed at the sensing electrode.

17. The device of claim 13 wherein the controller is further configured to cause the therapy delivery module to deliver the third pacing pulse by selecting the first anode and the second anode from a plurality of electrodes positioned along a single heart chamber.

18. The device of claim 13 wherein the first bipole is positioned along a heart chamber and the therapy delivery module is controlled by the controller to deliver the second pacing pulse by selecting the second anode as an electrode positioned away from the heart chamber.

19. The device of claim 13, wherein the controller is further configured to control the therapy delivery module to deliver at least one additional first pacing pulse and to determine a first capture threshold corresponding to the first bipole,
control the therapy delivery module to deliver at least one additional second pacing pulse and to determine a second capture threshold corresponding to the first cathode and the second anode, and
the controller further configured to determine a first capture threshold difference between the first capture threshold and the second capture threshold, wherein detecting anodal capture comprises detecting anodal capture in response to the first capture threshold difference.

20. The device of claim 19, wherein the controller is configured to measure the first capture threshold and the second capture threshold in response to the first difference being greater than a threshold.

21. A medical device for detecting anodal cardiac capture, comprising:
a plurality of electrodes for sensing cardiac signals and delivering cardiac pacing pulses;
a therapy delivery module for delivering cardiac pacing pulses to a patient's heart via the plurality of electrodes;
cardiac signal sensing circuitry for receiving signals from the plurality of electrodes; and
a controller configured to:
control the therapy delivery module to deliver a first pacing pulse using a first bipole comprising a first cathode and a first anode both positioned along a heart chamber and deliver a second pacing pulse using the first cathode and a second anode;
measure a first response of a received cardiac signal to the first pacing pulse;
measure a second response of the received cardiac signal to the second pacing pulse;
detect anodal capture of the heart chamber by the first pacing pulse at the first anode in response to a first difference between the first response and the second response;
control the therapy delivery module to deliver at least one additional first pacing pulse and to determine a first capture threshold corresponding to the first bipole, control the therapy delivery module to deliver at least one additional second pacing pulse and to determine a second capture threshold corresponding to the first cathode and the second anode, and the controller further configured to determine a first capture threshold difference between the first capture threshold and the second capture threshold, wherein detecting anodal capture comprises detecting anodal capture in response to the first capture threshold difference, wherein the controller is further configured to:

switch the polarity of the first anode to a cathode;

switch the polarity of the first cathode to an anode; and measure a third capture threshold corresponding to a second bipole comprising the first cathode switched to the anode polarity and the first anode switched to the cathode polarity wherein detecting anodal capture further comprises detecting anodal capture in response to the first capture threshold difference being greater than a second capture threshold difference between the first capture threshold and the third capture threshold.

22. The device of claim 13, wherein the controller is configured to measure the first response by measuring a first evoked response subsequent to the first pacing pulse and measure the second response by measuring a second evoked response subsequent to the second pacing pulse.

23. The device of claim 22, wherein measuring the first and second evoked responses comprises at least one of measuring a time interval from the respective first pacing pulse and the second pacing pulse to the respective sensed first evoked response and the second evoked response, and determining a morphological feature of the respective first and second evoked responses.

24. A medical device for detecting anodal cardiac capture, comprising:

a plurality of electrodes for sensing cardiac signals and delivering cardiac pacing pulses;

a therapy delivery module for delivering cardiac pacing pulses to a patient's heart via the plurality of electrodes;

cardiac signal sensing circuitry for receiving signals from the plurality of electrodes; and a controller configured to:

control the therapy delivery module to deliver a first pacing pulse using a first bipole comprising a first cathode and a first anode both positioned along a heart chamber and deliver a second pacing pulse using the first cathode and a second anode;

measure a first response of a received cardiac signal to the first pacing pulse;

measure a second response of the received cardiac signal to the second pacing pulse; and detect anodal capture of the heart chamber by the first pacing pulse at the first anode in response to a first difference between the first response and the second response, wherein the controller is further configured to measure a time to a first evoked response sensed at the first cathode and measure a time to a second evoked response sensed at the first anode;

responsive to the second evoked response occurring earlier than the first evoked response perform a capture threshold test to determine an anodal capture threshold and a cathodal capture threshold;

establish a pacing safety margin; and generate a warning of anodal capture in response to the cathodal capture threshold being more than the pacing safety margin greater than the anodal capture threshold.

25. A non-transitory computer-readable medium storing a set of instructions which when implemented in a medical device cause the device to perform a method for detecting anodal capture, the method comprising:

delivering a first pacing pulse using a first bipole comprising a first cathode and a first anode both positioned along a heart chamber;

delivering a second pacing pulse using the first cathode and a second anode;

measuring a first response to the first pacing pulse;

measuring a second response to the second pacing pulse;

detecting anodal capture of the heart chamber by the first pacing pulse at the first anode in response to a first difference between the first response and the second response;

switching the polarity of the first anode to a cathode;

delivering a third pacing pulse between the first anode switched to the cathode polarity and the second anode;

measuring a third response to the third pacing pulse; and detecting anodal capture in response to the first difference being greater than a second difference between the first response and the third response.

26. The method of claim 1, wherein the second anode is a coil electrode.

* * * * *